United States Patent
Rhodes

(10) Patent No.: US 6,704,957 B2
(45) Date of Patent: Mar. 16, 2004

(54) PATIENT SUPPORT PAD FOR MEDICAL IMAGING EQUIPMENT

(76) Inventor: Steven L. Rhodes, 1680 Dunn Ave., Unit 34, Jacksonville, FL (US) 32218

(*) Notice: Subject to any disclaimer, the term of this patent is extended or adjusted under 35 U.S.C. 154(b) by 0 days.

(21) Appl. No.: 10/210,670

(22) Filed: Jul. 31, 2002

(65) Prior Publication Data

US 2004/0019971 A1 Feb. 5, 2004

(51) Int. Cl.⁷ .................................................. A61F 5/00
(52) U.S. Cl. ................................. 5/637; 5/636; 5/639
(58) Field of Search ........................... 5/636, 637, 639, 5/622, 640, 630, 632, 633, 601

(56) References Cited

U.S. PATENT DOCUMENTS

| | | | | |
|---|---|---|---|---|
| 2,835,905 A | * | 5/1958 | Tomassson | 5/632 |
| 2,933,738 A | * | 4/1960 | Whelan | 5/630 |
| 4,206,524 A | * | 6/1980 | Cook | 5/630 |
| 4,400,820 A | | 8/1983 | O'Dell et al. | |
| 4,616,814 A | | 10/1986 | Harwood-Nash et al. | |
| 4,777,855 A | * | 10/1988 | Cohen | 5/636 X |
| 4,805,603 A | * | 2/1989 | Cumberland | 5/632 X |
| 4,979,519 A | | 12/1990 | Chavarria et al. | |
| 5,007,425 A | | 4/1991 | Vanek et al. | |
| 5,035,015 A | * | 7/1991 | Maietta | 5/630 |
| 5,095,569 A | * | 3/1992 | Glenn | 5/632 X |
| 5,166,618 A | | 11/1992 | Jones et al. | |
| 5,210,894 A | * | 5/1993 | Minton | 5/637 |
| 5,221,902 A | | 6/1993 | Jones et al. | |
| 5,305,750 A | | 4/1994 | Makita | |
| 5,361,765 A | | 11/1994 | Herlihy et al. | |
| 5,370,118 A | | 12/1994 | Vij et al. | |
| 5,519,907 A | * | 5/1996 | Poths | 5/636 |
| 5,577,503 A | | 11/1996 | Bonutti | |
| D403,194 S | * | 12/1998 | Thurston | D6/604 |
| 5,884,351 A | * | 3/1999 | Tonino | 5/636 X |
| D444,980 S | * | 7/2001 | Mowat et al. | 5/636 X |

* cited by examiner

*Primary Examiner*—Heather Shackelford
*Assistant Examiner*—Sunil Singh
(74) *Attorney, Agent, or Firm*—Thomas C. Saitta

(57) ABSTRACT

A pad for supporting the head and neck of a supine patient during medical imaging, wherein the pad produces either flexion or extension of the cervical vertebrae. A cavity is provided in the pad to define an area of non-contact on the back of the neck and to receive a secondary coil if present.

15 Claims, 3 Drawing Sheets

PATIENT SUPPORT PAD FOR MEDICAL IMAGING EQUIPMENT

BACKGROUND OF THE INVENTION

This invention relates generally to the field of medical devices used to support a portion of a patient's body in a desired position and alignment during a medical imaging procedure, such as a CAT scan or MRI. More particularly, the invention relates to any such devices which comprise pads, pillows or similar mechanisms which are configured to support the patient's spine or joints in either flexion or extension while the patient is supine on the gantry, platform or table of medical imaging equipment, and which further provide a recess or compartment for receiving secondary coils disposed adjacent the patient's body part of interest such that the secondary coils do not impart undesired flexion or extension of the body part.

A number of medical imaging devices utilizing x-rays, magnetic resonance imaging (MRI), computerized axial tomography (CAT) and the like are used in detecting, documenting and diagnosing injuries or defects in a patient's joints or spine. Such imaging devices are often utilized to diagnose spinal injuries or defects, such as traumatic hyperextension or hyperflexion resulting from accidents or the like. In the detection, analysis and diagnosis of such spinal conditions, and especially when the cervical vertebrae or neck region is of primary concern, it is often desirable to position the cervical vertebrae in a flexed or extended alignment during imaging. This is typically accomplished by providing concave or convex pillows or pads to reposition or support the patient's neck in a full flexion (vertebrae arched forward) or extension (vertebrae arched backward) position, which position the patient must maintain in a motionless manner during the imaging process. Such positions are uncomfortable and difficult to maintain for long periods of time, often leading to blurred imaging. Mechanical devices or support pads may also impart misalignment of the vertebrae, or may provide too much continuous support of the vertebrae, thus preventing imaging of lesions or aberrant motion of the vertebrae. In addition, where a secondary imaging coil, also called a localized, surface or volume coil, must be disposed adjacent the patient's neck, such as in MRI, the physical presence of the secondary coil itself interferes with or prevents the patient from being able to attain and maintain a desired flexion or extension position, or prevents lesions or aberrant motion from being documented. It has also been found that some pads and mechanical devices fail to produce a proper flexion position, in that the head and chin of the patient are angled forward but the vertebrae remain substantially linear.

Previous examples of devices or equipment which attempt to address the problems and issues inherent in achieving proper positioning of the spine or joints during medical imaging procedures include for example, U.S. Pat. No. 5,577,503 to Bonutti, U.S. Pat. No. 4,400,820 to O'Dell et al., U.S. Pat. No. 5,007,425 to Vanek et al., and U.S. Pat. No. 5,305,750 to Makita. The Bonutti patent shows an imaging table or gantry having various positioning structures built into the upper surface of the table that can be raised or lowered to support various portions of the patient's body in flexed or extended alignment as required. Because the positioning structures are of fixed location and configuration, the device is limited in its functionality and is not universally suitable as it fails to accommodate patients of different sizes. The positioning structures are hinged planar portions of the patient support table. Because the Bonutti apparatus is a table with integral components, the device does no offer a solution to the many imaging tables already in use. The O'Dell et al. patent shows a head cradle that requires strapping the patient's head into the device, which can result in less than optimum flexion or extension of the vertebrae, and the device does not address the problem of physical interference from secondary coils. The Vanek et al. patent shows a stand that can accommodate either a secondary coil or a portion of the patient's body, but does not address solutions to the problems discussed above. The Mikita patent shows a neck bending apparatus that also does not take into account the problems associated with misalignment from the secondary coil.

It is an object of this invention to provide a relatively uncomplicated device or set of related devices that address the problems discussed above in regard for attaining flexion and extension of the spine, and in particular the cervical spine, in a manner which is comfortable while providing sufficient support to immobilize the body portion during imaging, and further that provides a means to accommodate a secondary imaging coil such that the presence of the coil does not impart undesired alignment or misalignment in the spine during imaging. It is a further object to provide such a device or set of devices such that the device itself does not impart undesired alignment of the spine by providing too much continuous support, regardless of whether a secondary coil is utilized in the imaging process. It is a further object to provide such a device or devices having a material composition essentially invisible to the imaging equipment such that no artificial artifacts are created in the resulting images. These objects, as well as objects not expressly set forth but which will become apparent upon understanding of the disclosure to follow, are supported by the disclosure to follow.

SUMMARY OF THE INVENTION

The invention comprises a support pad or pillow, individually or comprising a set, for supporting a patient during a medical imaging procedure, and in particular for supporting the cervical vertebrae or neck area of the patient in a manner which provides for flexion or extension when the patient is supine on the table of the medical imaging equipment. The invention is suitable for use with various types of medical imaging equipment, including for example x-ray, magnetic resonance imaging (MRI), or computerized axial tomography (CAT). In particular, the invention solves problems inherent in medical imaging equipment that requires a secondary coil to be affixed to or positioned adjacent the patient's neck.

The invention comprises a pad of sufficient rigidity to support the weight of a patient's head, yet with some degree of cushioning effect for comfort. The pad comprises a curved support surface and a generally rectangular cavity. For disposing the cervical vertebrae in extension, the curved support surface is arched outward. For disposing the cervical vertebrae in flexion, the curved support surface is depressed inward, with one end of the pad significantly higher than the other. A depression to receive or cradle the rear of the patient's head is provided above the cavity on the flexion pad. The cavity is disposed on the support surface of both the flexion and extension pad and provides an area of non-contact on the back of the neck such that the tissue and vertebrae are not excessively supported in a continuous manner to preclude or hinder documentation of lesions or aberrant motion, or are not distorted or misaligned by pressure from the support surface itself. The cavity further provides a space to receive a secondary coil if present, such that the coil does not interfere with the desired alignment or prevent detection of lesions or aberrant motion. The flexion and extension pads form a diagnostic imaging set, in that it is often desirable to image the vertebrae in both flexion and extension.

An alternative embodiment is also provided, wherein the extension pad can be used alone to provide extension, but also becomes a base to receive and support a flexion pad. In one embodiment, a groove is provided in the support surface of the extension pad and a corresponding tongue is provided on the underside of the flexion pad, such that the flexion pad can be interlocked with the extension pad when flexion imaging is desired.

DETAILED DESCRIPTION OF THE INVENTION

With reference to the drawings, the invention will now be described in detail with regard for the best mode and the preferred embodiment. In a most general sense, the invention is a support pad or pillow device for supporting the head and neck of a supine patient during medical imaging procedures such that the cervical vertebrae are disposed in flexion or extension as desired. The pad provides a stable supportive surface yet imparts the correct vertebral alignment, and is formed of a material that is invisible or non-interfering to the imaging equipment, such that false artifacts are not created by the pad itself. The vertebrae are in extension when the head is angled back and the cervical vertebrae are arched to the front, and the vertebrae are in flexion when the head is angled forward and the cervical vertebrae are arched to the rear. The pads are preferably provided as a set such that imaging may be accomplished in both the flexion and extension positions. The invention is suitable for use with various types of medical imaging equipment, including for example x-ray, magnetic resonance imaging (MRI), or computerized axial tomography (CAT).

As used herein, references to the inferior direction shall be taken to be that direction toward the feet of the patient when the invention is in use, and references to the superior direction shall be taken to be the direction toward the head of the patient.

The invention is most preferably composed of materials that are invisible to the imaging equipment so as not to create false artifacts or images, or if not invisible at least composed of materials which produce non-interfering images of reduced or minimal appearance. The pads should be relatively sturdy and durable, and must have sufficient rigidity or denseness such that the head and neck of the patient are supported in the desired position with only a small amount of compression, thus insuring that movement of the head and neck is kept to a minimum during imaging. The outer surface may be composed of a plastic or cloth material, and a removable cover may be provided.

Figure 1:
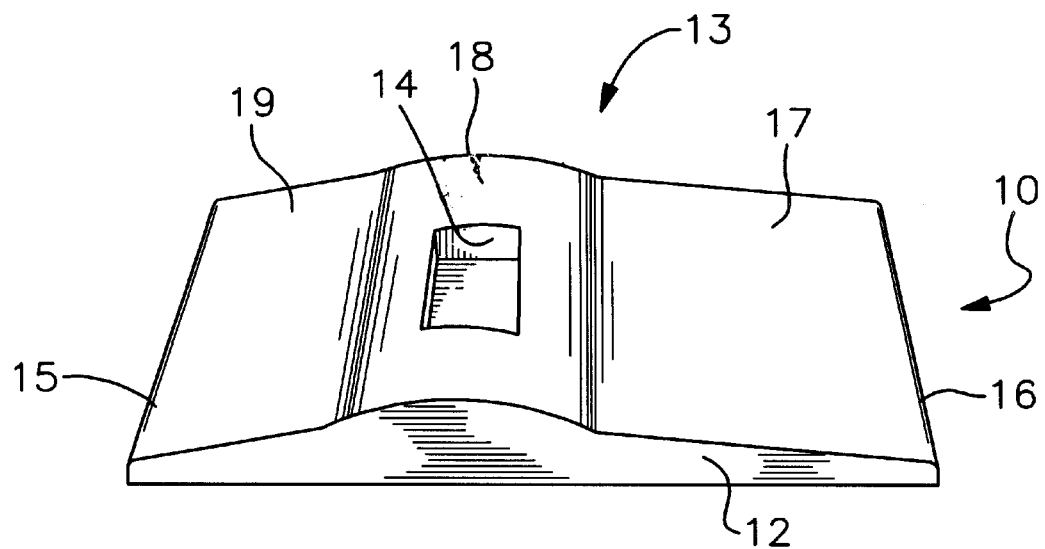
FIG. 1 is a perspective view of the pad of the invention in the embodiment for imparting extension to the cervical spine.
Figure 2:
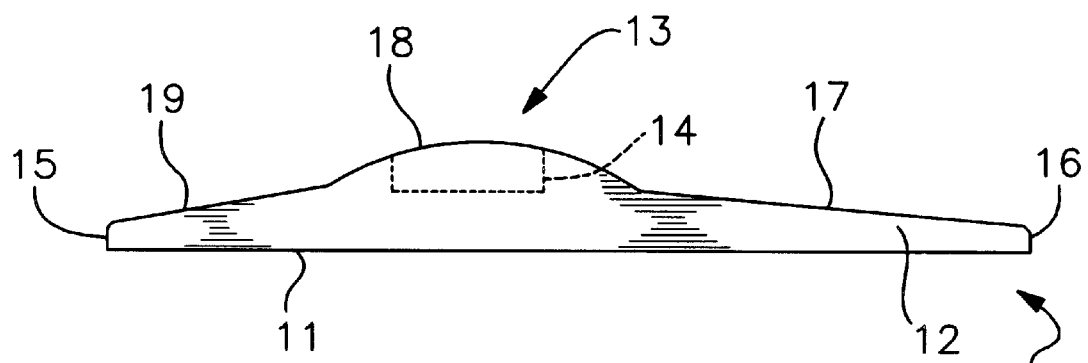
FIG. 2 is a side view of the embodiment of FIG. 1.

As shown in FIGS. 1 and 2, the pad 10 as adapted for extension of the cervical vertebrae comprises a generally rectangular, flat bottom surface 11, side walls 12, a curved upper support surface 13, and a cavity 14. The upper support surface 13 is arched or convex in longitudinal cross-section such that the apex or thickest portion of the extension pad 10 is in an arched or humped intermediate portion between the superior end 15 and the inferior end 16. The superior and inferior ends 15 and 16 are of limited or relatively minimal height, such that the extension pad 10 tapers in both longitudinal directions, to provide a comfortable transition from the table surface of the imaging equipment to the upper support surface 13. Thus the upper support surface 13 is preferably divided into a generally planar, preferably slanted, inferior segment 17, an intermediate arched segment 18 and a generally planar, preferably slanted, superior segment 19. For example, an extension pad 10 of approximately 20 inches in length will preferably have a height of about 4 inches at the apex of the intermediate arched segment 18, while the superior and inferior ends 15 and 16 are preferably less than an inch in height.

The cavity 14 is positioned in the intermediate arched segment 18, preferably slightly toward the superior end 15, and is preferably sized approximately 6 inches by 6 inches with a depth of approximately 1 inch in order to provide sufficient space for non-contact with the neck area corresponding to the segments of the cervical vertebrae of interest, and to provide a recessed area to receive a secondary coil positioned on the patient, such as when HI is the imaging technique, such that the secondary coil is not pressed against the patient's neck by the pad resulting in misalignment of the vertebrae. A slot 90 may be extended from the cavity 14 to one or both of the side walls 12 to provide an access conduit.

In use, the extension pad 10 is positioned so that the shoulders of the patient are supported by the slanted inferior segment 17, the neck of the patient is supported by the intermediate arched segment 18, the neck extending across the cavity 14, and the head of the patient is supported by the slanted superior segment 19. The patient's head may be strapped to minimize motion during the imaging process.

Figure 3:
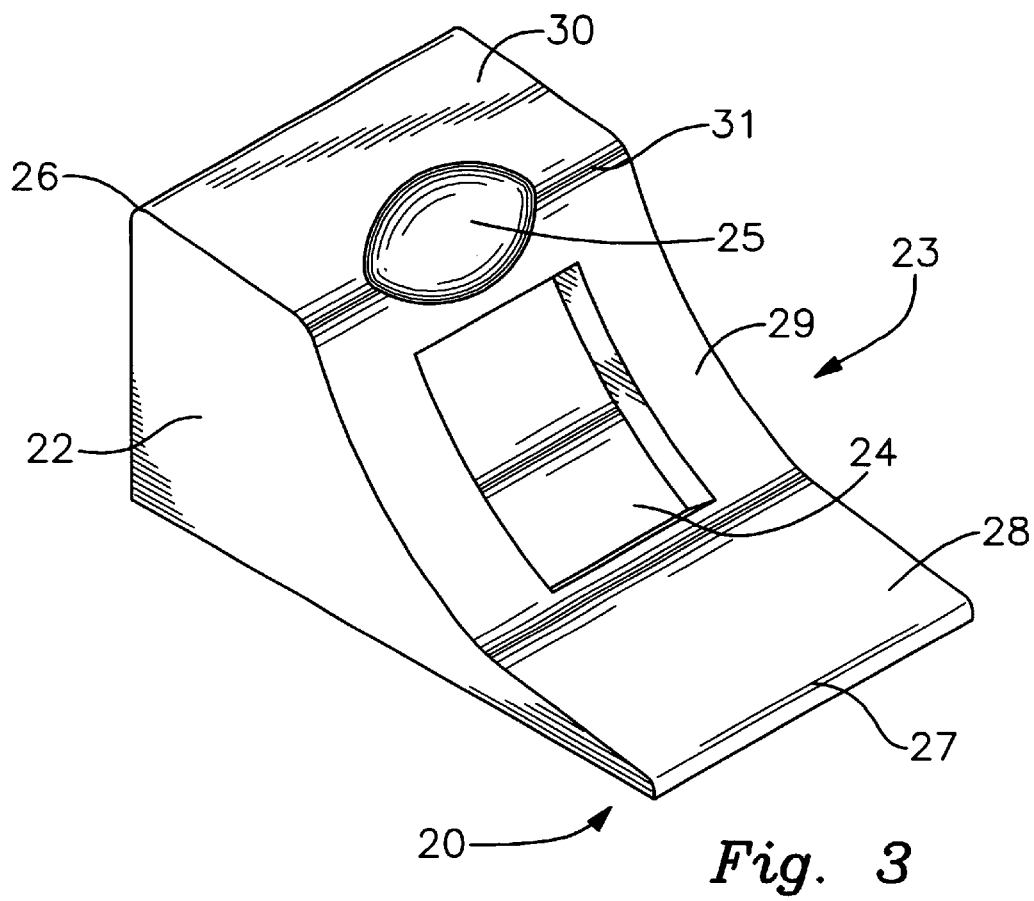
FIG. 3 is a perspective view of the pad of the invention in the embodiment for imparting flexion to the cervical spine.
Figure 4:
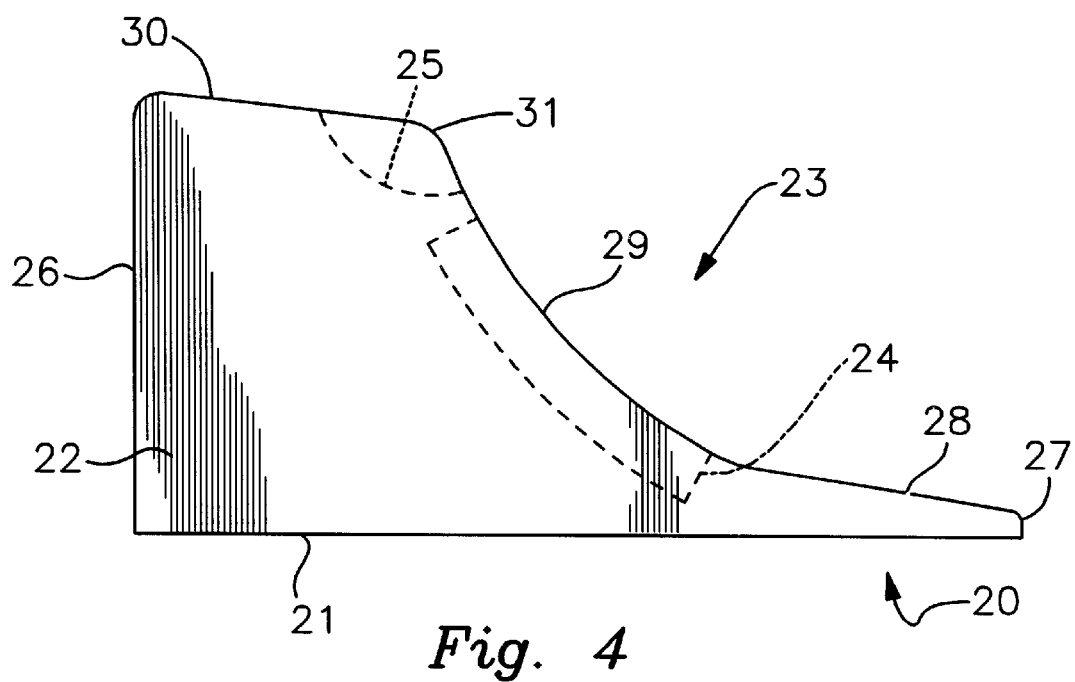
FIG. 4 is a side view of the embodiment of FIG. 3.

As shown in FIGS. 3 and 4, the pad 20 as adapted for flexion of the cervical vertebrae comprises a generally rectangular, flat bottom surface 21, side walls 22, a curved upper support surface 23, a cavity 24 and a cranial depression 25 for receiving the back of the patient's head. The upper support surface 23 is negatively arched or concave in longitudinal cross-section. The superior end 26 is of much greater relative height as compared to the inferior end 27, which is of limited or relatively minimal height, such that the flexion pad 20 tapers down in the inferior direction to define a generally L-shaped configuration when viewed from the side, to provide a comfortable transition from the table surface of the imaging equipment to the upper support surface 23. Thus the upper support surface 23 is preferably divided into a slanted, generally planar or slightly curved, inferior segment 28, an intermediate curved segment 29, and a slightly slanted or generally horizontal, generally planar superior shoulder segment 30. For example, a flexion pad 20 of approximately 20 inches in length will preferably have a height of about 10 inches at the superior end 26, while the inferior end 16 is preferably less than an inch in height. The superior shoulder segment 30 will preferably extend about 10 inches from the superior end 26.

The cavity 24 is positioned in the intermediate curved segment 29, a few inches below the junction 31 between the superior shoulder segment 30 and the intermediate curved segment 29, and is preferably sized approximately 6 inches by 6 inches with a depth of approximately 1 inch in order to provide sufficient space for non-contact with the neck area corresponding to the segments of the cervical vertebrae of interest, and to provide a recessed area to receive a secondary coil positioned on the patient, such as when MRI is the imaging technique, such that the secondary coil is not pressed against the patient's neck by the flexion pad 20 resulting in misalignment of the vertebrae. A slot 90 may be extended from the cavity 24 to one or both of the side walls 22 to provide an access conduit.

A cranial depression 25 is disposed centrally along the junction 31 between the superior shoulder segment 30 and the intermediate curved segment 29 and is provided preferably with a curved, concave configuration adapted to receive the back of the patient's head in a manner which restricts lateral movement. Preferably the cranial depression is approximately 6 inches in the lateral dimension and extends approximately 3 inches to either side of the junction 31.

In use, the flexion pad 20 is positioned so that the shoulders of the patient are supported by the slanted inferior segment 28 and the head of the patient is supported by the cranial depression 25, such that the neck of the patient extends across the cavity 24. The patient's head may be strapped to minimize motion during the imaging process.

Figure 6:
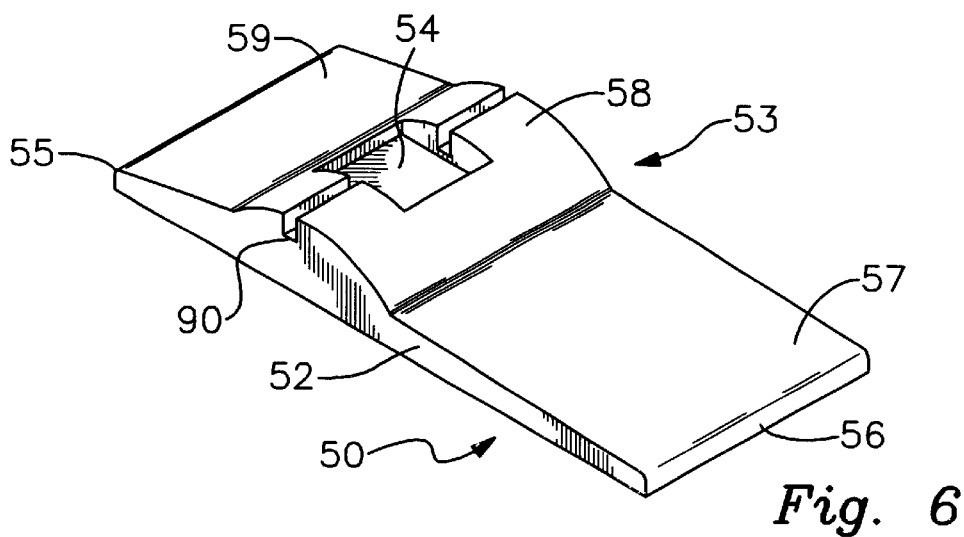
FIG. 6 is a perspective view of the base extension pad of the embodiment of FIG. 5.
Figure 7:
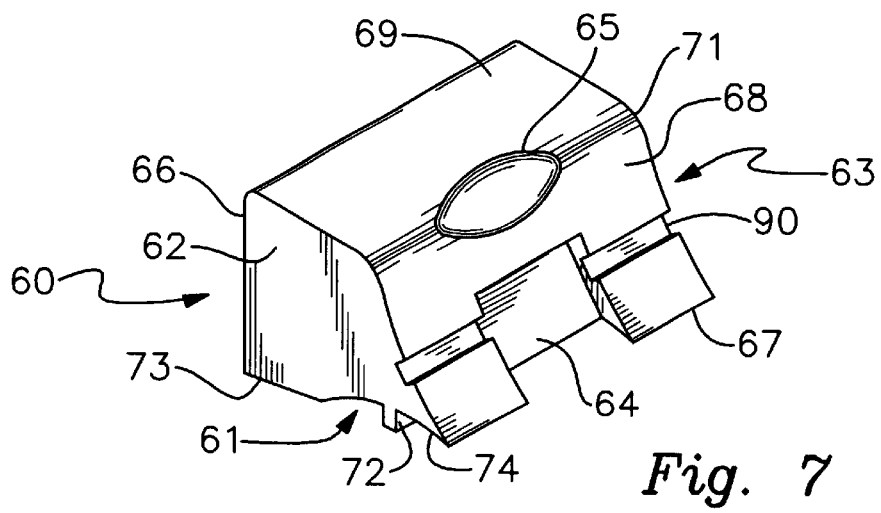
FIG. 7 is a perspective view of the upper flexion pad of the embodiment of FIG. 5.

In practice the extension pad 10 and the flexion pad 20 as described will comprise a set of pads available during medical imaging such that both the flexion and extension positions can be obtained by proper selection. In an alternative embodiment of the invention shown in FIGS. 5 through 7, a base extension pad 50 and flexion adaptor pad 60 together define a combination imaging pad 40. Interlocking means 41 temporarily secure the flexion adaptor pad 60 atop the base extension pad 50 when the flexion position is required. When the extension position is required, the flexion adaptor pad 60 is removed and the base extension pad 50 is used alone.

The base extension pad 50 is preferably substantially similar if not identical to the extension pad 10 shown in FIGS. 1 and 2 and described above. The base extension pad 50 comprises a generally rectangular, flat bottom surface 51, side walls 52, a curved upper support surface 53, and a cavity 54. The upper support surface 53 is arched or convex in longitudinal cross-section such that the apex or thickest portion of the base extension pad 50 is in an arched or humped intermediate portion between the superior end 55 and the inferior end 56. The superior and inferior ends 55 and 56 are of limited or relatively minimal height, such that the base extension pad 50 tapers in both longitudinal directions, to provide a comfortable transition from the table surface of the imaging equipment to the upper support surface 53. Thus the upper support surface 53 is divided into a slanted, relatively planar inferior segment 57, an intermediate arched segment 58 and a slanted, relatively planar superior segment 59.

The cavity 54 is positioned in the intermediate arched segment 58, preferably slightly toward the superior end 55, and is preferably sized approximately 6 inches by 6 inches with a depth of approximately 1 inch in order to provide sufficient space for non-contact with the neck area corresponding to the segments of the cervical vertebrae of interest, and to provide a recessed area to receive a secondary coil positioned on the patient, such as when MRI is the imaging technique, such that the secondary coil is not pressed against the patient's neck by the pad resulting in misalignment of the vertebrae. Interlocking means 41 for temporarily securing the base extension pad 50 to the flexion adaptor pad 60 are provided, and may comprise any suitable mechanical interlocking structures, fasteners or other co-joining mechanisms. As shown, interlocking means 41 comprises a slot 90 extended transversely across the cavity 54 to both of the side walls 12, the slot 90 sized to receive the tongue member 72 of the flexion adaptor pad 60.

The flexion adaptor pad 60 is preferably substantially similar to the flexion pad 20 shown in FIGS. 3 and 4 and described above, except in the structure of its inferior end 67 and its bottom surface 61. The flexion adaptor pad 60 comprises a bottom surface 61, side walls 62, a curved upper support surface 63, a cavity 64 and a cranial depression 65 for receiving the back of the patient's head. The upper support surface 63 is negatively arched or concave in longitudinal cross-section. The superior end 66 is of much greater relative height as compared to the inferior end 67, which is of limited or relatively minimal height. The upper support surface 63 is divided into a curved inferior segment 68 and a slightly slanted or generally horizontal, relatively planar superior shoulder segment 69.

The cavity 64 is positioned in the inferior curved segment 68, a few inches below the junction 71 between the superior shoulder segment 69 and the inferior curved segment 68, and is preferably sized approximately 6 inches by 6 inches with a depth of approximately 1 inch in order to provide sufficient space for non-contact with the neck area corresponding to the segments of the cervical vertebrae of interest, and to provide a recessed area to receive a secondary coil positioned on the patient, such as when MRI is the imaging technique, such that the secondary coil is not pressed against the patient's neck by the flexion adaptor pad 60 resulting in misalignment of the vertebrae. A slot 90 may be extended from the cavity 64 to one or both of the side walls 62 to provide an access conduit.

A cranial depression 65 is disposed centrally along the junction 71 between the superior shoulder segment 69 and the inferior curved segment 68 and is provided preferably with a curved, concave configuration adapted to receive the back of the patient's head in a manner which restricts lateral movement.

Figure 5:
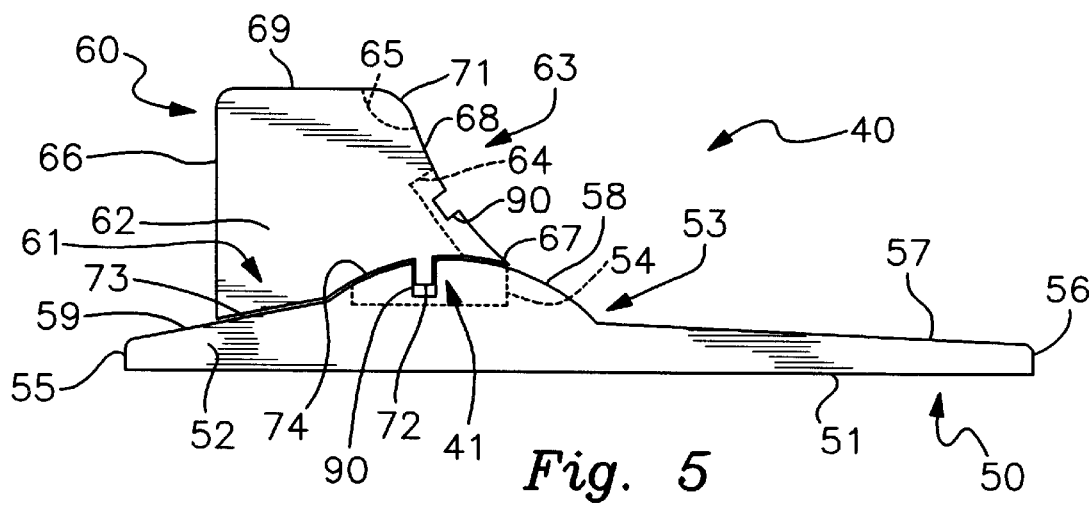
FIG. 5 is a side view of an alternative embodiment of the invention, wherein the invention comprises a pair of interrelated pads capable of imparting flexion or extension to the cervical spine.

The bottom surface 61 of the flexion adaptor pad 60 comprises a bottom curved segment 74 and a bottom slanted segment 73. The bottom slanted segment 73 corresponds in configuration to the slanted superior segment 59 of the upper support surface 53 of the base extension pad 50, and the bottom curved segment 74 corresponds in configuration to the intermediate arched segment 58 of the base extension pad 50, such that the flexion adaptor pad 60 can be disposed on the base extension pad 50 as shown in FIG. 5. Interlocking means 41 are provided to temporarily secure the pads 50 and 60 from unwanted shifting, and as shown comprises a tongue member 72 depending from the bottom surface 61 which mates with the slot 90 in the upper support surface 53 of the base extension pad 50. In this manner, the slanted superior segment 57 and a portion of the intermediate arched segment 58 in combination with the flexion adaptor pad 60 form a configuration similar to the configuration of the flexion pad 20,the exposed upper support surface 53 of the base extension pad 50 being positioned beneath the shoulders of the patient while the head of the patient is supported by the flexion adaptor pad 60 when the flexion position is required.

It is contemplated that certain equivalents or substitutions for components set forth above may become obvious to those skilled in the art, and therefore the true scope and definition of the invention is to be as set forth in the following claims.

I claim:

1. A pad for supporting the head and neck of a supine patient during medical imaging such that extension of the cervical vertebrae is produced, said pad comprising:

a curved upper support surface comprising a slanted and generally planar inferior segment of sufficient size and adapted to support a patient's shoulders, a slanted and generally planar superior segment of sufficient size and adapted to support a patient's head, and an intermediate arched segment disposed between said inferior segment and said superior segment of sufficient size and adapted to support a patient's neck; and a cavity disposed in said intermediate arched segment of said upper support surface, said cavity adapted to provide an area of non-contact to a portion of a patient's neck and to receive a secondary coil of a medical imaging apparatus;

whereby the combination of said inferior segment, said superior segment and said intermediate segment of said support surface of said pad produces extension of a patient's cervical vertebrae.

2. The pad of claim 1, wherein said cavity is generally rectangular.

3. The pad of claim 1, said pad further comprising a superior end and an inferior end, wherein said superior end and said inferior end are each less than approximately one inch in height, and said intermediate arched segment is approximately four inches in height.

4. A pad for supporting the head and neck of a supine patient during medical imaging such that flexion of the cervical vertebrae is produced, said pad comprising:

a curved upper support surface comprising a slanted inferior segment sufficiently sized and adapted to support a patient's shoulders, a superior shoulder segment; and an intermediate curved segment disposed between said inferior segment and said superior shoulder segment sufficiently sized and adapted to support a patient's neck, said intermediate curved segment being concave;

a junction between said intermediate curved segment and said superior shoulder segment, and a cranial depression disposed on said junction sufficiently sized and adapted to receive a patient's head, and a cavity disposed in said intermediate curved segment of said upper support surface, said cavity adapted to provide an area of non-contact to a portion of a patient's neck and to receive a secondary coil of a medical imaging apparatus;

whereby the combination of said inferior segment, said superior segment and said intermediate segment of said support surface of said pad produces flexion of a patient's cervical vertebrae.

5. The pad of claim 4, wherein said cavity is generally rectangular.

6. The pad of claim 4, said pad further comprising a superior end and an inferior end, wherein said superior end is of greater height than said inferior end, and said inferior end is less than approximately one inch in height.

7. A pad for supporting a patient's head and neck during medical imaging such that either flexion or extension of the cervical vertebrae is produced, said pad comprising in combination:

a base extension pad and a removable flexion adaptor pad;

said base extension pad comprising a generally flat bottom surface, a curved upper support surface capable of producing extension in cervical vertebrae, and a cavity disposed in said upper support surface, said cavity adapted to provide an area of non-contact to a portion of a patient's neck and to receive a secondary coil of a medical imaging apparatus;

said flexion adaptor pad comprising a bottom surface corresponding to a portion of said upper support surface of said base extension pad, a curved upper support surface capable of producing flexion in cervical vertebrae, and a cavity disposed in said upper support surface, said cavity adapted to provide an area of non-contact to a portion of a patient's neck and to receive a secondary coil of a medical imaging apparatus;

whereby said flexion adaptor pad is removed from said base extension pad to produce extension, and whereby said flexion adaptor pad in combination with said base extension pad are used to produce flexion.

8. The pad of claim 7, wherein said bottom surface of said flexion pad comprises a curved segment and a slanted segment.

9. The pad of claim 7, further comprising interlocking means to temporarily secure said flexion adaptor pad to said base extension pad.

10. The pad of claim 9, wherein said interlocking means comprises in combination a slot disposed on said upper support surface of said base extension pad and a tongue member disposed on said bottom surface of said flexion adaptor pad.

11. A combination set of a pads for supporting the head and neck of a supine patient during medical imaging such that either extension or flexion of the cervical vertebrae is produced dependent upon which pad is chosen, the set comprising:

(A) a first pad comprising a curved upper support surface comprising a slanted and generally planar inferior segment of sufficient size and adapted to support a patient's shoulders, a slanted and generally planar superior segment of sufficient size and adapted to support a patient's head, and an intermediate arched segment disposed between said inferior segment and said superior segment of sufficient size and adapted to support a patient's neck; and a cavity disposed in said intermediate arched segment of said upper support surface, said cavity adapted to provide an area of non-contact to a portion of a patient's neck and to receive a secondary coil of a medical imaging apparatus;

whereby the combination of said inferior segment, said superior segment and said intermediate segment of said support surface of said pad produces extension of a patient's cervical vertebrae; and (B) a second pad comprising a curved upper support surface comprising a slanted inferior segment sufficiently sized and adapted to support a patient's shoulders, a superior shoulder segment; and an intermediate curved segment disposed between said inferior segment and said superior shoulder segment sufficiently sized and adapted to support a patient's neck, said intermediate curved segment being concave;

a junction between said intermediate curved segment and said superior shoulder segment, and a cranial depression disposed on said junction sufficiently sized and adapted to receive a patient's head, and a cavity disposed in said intermediate curved segment of said upper support surface, said cavity adapted to provide an area of non-contact to a portion of a patient's neck and to receive a secondary coil of a medical imaging apparatus;

whereby the combination of said inferior segment, said superior segment and said intermediate segment of said support surface of said pad produces flexion of a patient's cervical vertebrae.

12. The set of claim 11, wherein said first pad cavity and said second pad cavity are generally rectangular.

13. The set of claim 11, said first pad further comprising a superior end and an inferior end, wherein said superior end and said inferior end are each less than approximately one inch in height, and said intermediate arched segment is approximately four inches in height.

14. The set of claim 13, said second pad further comprising a superior end and an inferior end, wherein said superior end is of greater height than said inferior end, and said inferior end is less than approximately one inch in height.

15. The set of claim 11, said second pad further comprising a superior end and an inferior end, wherein said superior end is of greater height than said inferior end, and said inferior end is less than approximately one inch in height.

* * * * *